United States Patent [19]

Koeneman et al.

[11] Patent Number: 4,750,905
[45] Date of Patent: Jun. 14, 1988

[54] BEAM CONSTRUCTION AND METHOD

[75] Inventors: James Koeneman, Mesa; Thomas Hansen; Ron Yapp, both of Phoenix; Allan M. Weinstein, Paradise Valley; Roger Johnson, Phoenix, all of Ariz.

[73] Assignee: Harrington Arthritis Research Center, Phoenix, Ariz.

[21] Appl. No.: 830,856

[22] Filed: Feb. 19, 1986

Related U.S. Application Data

[63] Continuation-in-part of Ser. No. 753,711, Jul. 10, 1985.

[51] Int. Cl.⁴ ............................ A61F 2/28; A61F 2/32
[52] U.S. Cl. ...................................... 623/16; 623/22; 623/23
[58] Field of Search ................ 273/DIG. 7, DIG. 23, 273/80 B; 623/23, 16, 17, 18, 19, 20, 21, 22, 23, 13

[56] References Cited

U.S. PATENT DOCUMENTS

| 3,683,422 | 8/1972 | Stemmer et al. ................. 623/18 X |
| 3,893,196 | 7/1975 | Hochman . |
| 3,953,637 | 4/1976 | Phillips .................... 273/DIG. 23 X |
| 4,127,902 | 12/1978 | Homsy ............................... 623/16 X |
| 4,221,623 | 9/1980 | Heissler et al. .................... 623/23 X |
| 4,512,038 | 4/1985 | Alexander et al. ............... 623/16 X |
| 4,589,883 | 5/1986 | Kenna . |
| 4,650,489 | 3/1987 | Thompson . |

FOREIGN PATENT DOCUMENTS

| 0007287 | 1/1980 | European Pat. Off. .............. 623/22 |
| 0006414 | 1/1980 | European Pat. Off. .............. 623/22 |
| 2636644 | 2/1978 | Fed. Rep. of Germany ........ 623/22 |
| 2708917 | 9/1978 | Fed. Rep. of Germany ........ 623/22 |
| 2935511 | 3/1981 | Fed. Rep. of Germany ........ 623/22 |
| 85/04323 | 10/1985 | PCT Int'l Appl. . |

OTHER PUBLICATIONS

"The Use of Polymers for Endoprosthetic Components", by Mathys et al.
Early Results of the RM-Isoelastic Cementless Total Hip Prosthesis: 300 Consecutive Cases with 2-Year Follow-Up, by Bombelli et al.

*Primary Examiner*—Richard J. Apley
*Assistant Examiner*—Alan W. Cannon
*Attorney, Agent, or Firm*—Vidas & Arrett

[57] ABSTRACT

An improved prosthesis construction in a femoral-side hip joint replacement device of the type having an elongate curved stem held within an intramedullary cavity in a femur, and a neck supporting a ball-like joint member at the femur's proximal end. The construction includes an elongate polymer core containing continuous-filament fibers oriented substantially along the length of the core. The core contains the neck, an elongate distal stem whose cross-sectional area is less than about one-quarter that of the neck, and a tapered sections which mates the neck to the stem. A polymer skin fused to and covering the stem and tapered section of the core is shaped and dimensioned to conform to and fill the bone cavity. A braided sheath encases the stem and tapered sections of the core and it embedded in the polymer skin adjacent the core. The filaments which made up the braid in the sheath encircle the core in a helical pattern extending along the stem and tapered section provided resistance to torsional stresses on the stem. Also disclosed are novel methods for making the prosthesis construction.

15 Claims, 2 Drawing Sheets

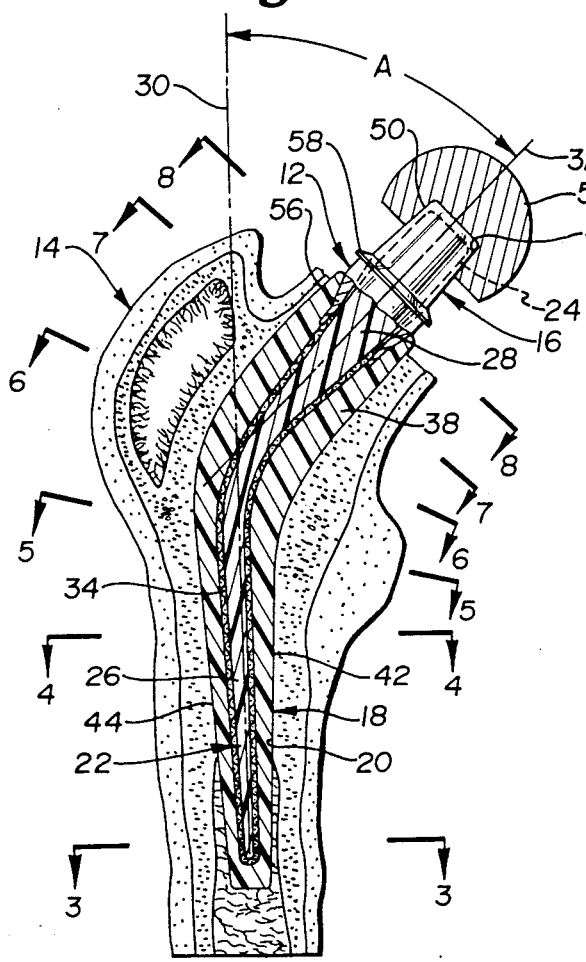
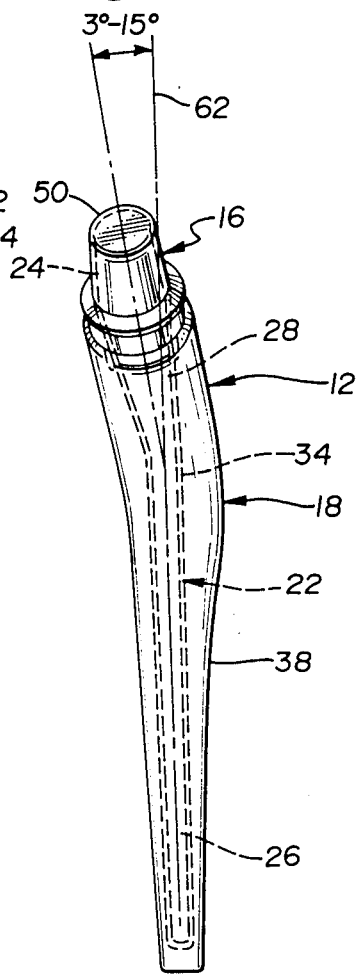
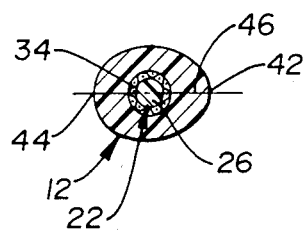
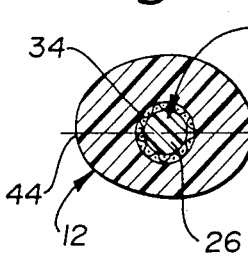
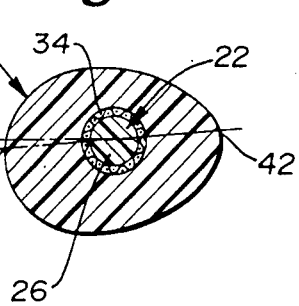

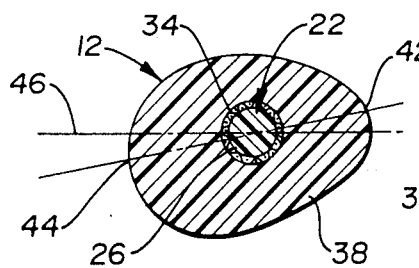
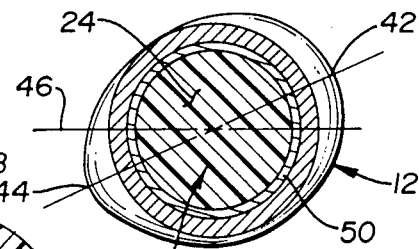
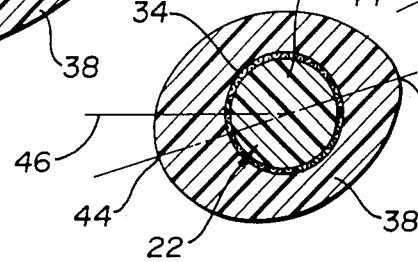
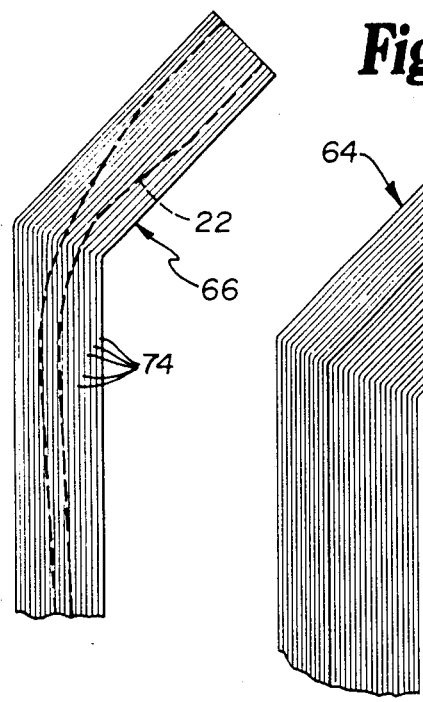
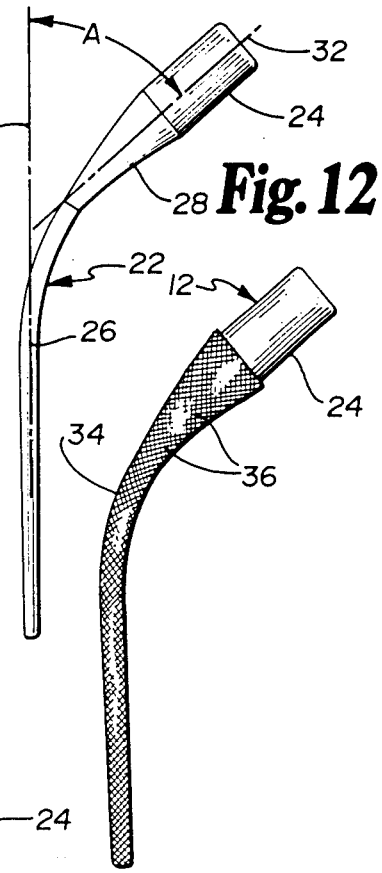
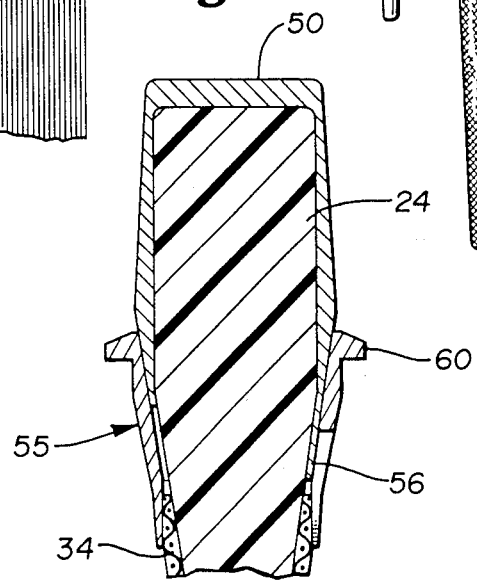

BEAM CONSTRUCTION AND METHOD

This application is a continuation-in-part of co-pending U.S. patent application Ser. No. 753,711, filed July 10, 1985, for "Femoral-Joint Prosthetic Device".

FIELD OF THE INVENTION

The present invention relates to an improved beam construction and method, and particularly, to a beam construction for use in a load-bearing joint-replacement prosthetic device.

BACKGROUND OF THE INVENTION

Structural beams which can withstand both bending and torsion loads are useful in a variety of applications, including industrial, aerospace, and orthopedic uses. One type of structural beam which has received considerable attention in the orthopedic field is a hip-joint replacement device. In basic design, this device includes an elongate curved stem which is adapted for receipt in a cavity formed in the proximal region of a femur, and a ball-like joint member carried on a neck at the upper end of the stem. When implanted in operative position, the device functions as a load transfer member between the pelvis and femur, and as such, must accommodate considerable bending, axial compression and torsional forces applied across the joint to the femur.

Three basic constructions have been proposed hereafter for hip-joint devices of this type. In all of these constructions, the curved stem, which is adapted for insertion into a bone cavity, and the neck, which is adapted to support the ball-like joint member, are formed as a single piece, and the joint member is separately attached to the neck, preferably after inserting the stem into the bone. In one construction the stem and neck are formed as a unitary metal piece from stainless steel or, more preferably, from a titanium alloy. An advantage of an all-metal construction is that the relatively thick metal stem and neck provide adequate bending and shear strength, so that problems of stem fracture or fatigue are minimal. A disadvantage of the construction is a high degree of weight loading stress on certain regions of the bone, and stress protection in other bone regions. Both high stress and stress protection can cause bone deterioration and resorption, leading to areas of bone weakness and loss of bone support for the prosthesis.

The related problems of bone stress and stress protection which can occur in a hip-joint replacement can be understood from the mechanics of weight load transfer across the hip-joint device. Normally, much of the weight load is transferred to the femur near the upper joint region and this load is distributed to and carried by the underlying cortical bone region and the prosthesis stem. The distribution of forces in the underlying cortical region and prosthesis stem region is determined by the relative stiffness—or elastic modulus—of the bone and stem respectively. In normal bone, the elastic modulus of the outer cortical bone region is about 2.5, and that of the softer interior cancellous region is less than 1, so that weight loading forces are carried primarily by the outer cortical region. By contrast, the metal stem region of a prosthetic device, which replaces the soft cancellous region of bone, has an elastic modulus typically between about 15-35, so that much more weight loading is carried by the stem, and much less by the outer cortical bone. In addition to the stress protection this produces in the bone region adjacent the stem, the high-modulus stem also produces unnaturally high bone stress at the lower tip of the stem, where forces carried in the stem are transmitted to the bone.

In a second known prosthesis construction, the stem and neck are formed from rolled or laminated layers of a composite material containing oriented carbon fibers embedded in a polymer resin. This construction is described generally in PCT patent application for "Orthopedic Device and Method of Making Same", WO No. 85/04325, filed Mar. 29, 1985. In a preferred embodiment, a series of composite layers containing fibers oriented in different directions are laminated, according to known composite block construction methods, to produce a machinable block whose different fiber orientations confer strength in different, selected directions with respect to the long axis of the block. The laminated block is then machined to produce a stem and neck piece which can be implanted in bone and fitted with a ball-like joint member. Since the laminate structure has a somewhat lower average elastic modulus, both in tension and shear, then a comparable-size metal prosthesis, the above problems related to stress protection along the length of the prosthesis stem, and the high concentration of forces at the lower tip of the stem are somewhat reduced. However, the effective elastic moduli of the stem in tension and shear is still very high compared with the soft cancellous region of bone which the stem has replaced. Furthermore, the laminate material is generally not as strong as a comparable-size metal stem, particularly at the neck region of the device where weight loading is borne entirely by the prosthesis. This is due in part to the fact that the carbon fibers oriented lengthwise in the stem do not follow the curvature of the stem, and generally do not extend along the entire length of the stem.

A third prothesis construction which has been proposed in the prior art involves a metal core having a relatively large-diameter neck and small-diameter stem which is encased in a low-modulus polymer. A prosthesis of this type is described by Mathis, R., Jr., et al in "Biomechanics: Current Interdisciplinary Research" (Perren, M., et al, eds.) Martinus Nijhoff, Boston (1985) pp. 371-376. The combined modulus of the polymer and inner core of the device is much more like that of interior cancellous bone than is either a solid metal or laminate composite structure, and as a result, problems related to bone stress protection and high stress are reduced. This compound device has not been entirely satisfactory, however. One problem which has been encountered is fracturing at the neck/stem interface, due to large loading force applied at this juncture by the neck. A second problem is related to the cutting action of the relatively stiff metal core against the low-modulus polymer, in response to forces exerted on the stem in directions normal to the stem's long axis. Over an extended period, the cutting action can lead to core wobbling within the bone, and exaggerated movement of the core in response to loading.

Another general problem which has been encountered in prior art hip-joint replacement devices is poor seating and fixation of the stem in the bone cavity. This problem has been discussed at length in the above-cited copending patent application. Briefly, the size and shape of prior art hip prosthesis devices requires removal of a substantial amount of hard outer cortical bone in forming the stem-receiving cavity, and this can weaken the bone structure and reduce blood supply to the proximal femur. In addition, the relatively large prosthesis cross section and lack of natural bone support for the prosthesis makes it difficult to anchor the prosthesis by press fit in the cavity. As a result, the stem may work loose in time, due to torsional stresses.

SUMMARY OF THE INVENTION

One object of the invention, therefore, is to provide a curved-stem hip-joint replacement device which substantially overcomes or reduces above-noted problems associated with known hip-joint devices.

A more general object of the invention is provide an improved beam for supporting a load capable of applying bending and torsional loading forces.

It is yet another object of the invention to provide a method for forming such a prosthetic device, and more generally, the novel load-bearing beam.

The present invention includes an elongate beam which is designed to support a load capable of applying both bending and torsional load forces. An important application of the beam is for use as a joint-replacement prosthetic device, and particularly a hip-joint replacement prosthetic device, in which major weight-loading axial compression forces are applied to the beam in bending and torsion.

The beam generally includes an elongate composite core formed of continuous-filament fibers oriented substantially along the length of the core and embedded in a polymer matrix. Where the core has a curved stem, such as in a hip-joint replacement device, the fibers extend in a substantially uniform-density, non-distorted configuration from one end of the core to the other. The core is characterized by high tensile strength and elastic modulus, but relatively low shear strength and modulus. The core in an exemplary hip-joint prosthesis has a neck adapted for supporting a ball-like joint member, an elongate distal stem whose cross-sectional area is less than about one-quarter that of the neck, and a tapered section which mates the neck to the stem and whose length is substantially less than that of the stem.

The core is encased in a sheath which, in an exemplary hip-prosthesis device, encases the stem and tapered section of the core, but not its upper neck. The sheath is made up of braided or woven filaments which encircle the stem in a helical pattern extending along the encased portion of the core. The sheath filaments are bonded to the core by a thermoplastic polymer which are infused into the sheath and heat fused to the core. Thus bonded to the core, the filaments in the sheath provide the core with high shear strength and stiffness for resisting torsional loading. At the same time the core and sheath have a relatively low stiffness to forces directed against the core in a direction normal to the core's long axis, minimizing the tendency of the core to cut into the polymer.

The polymer which embeds and bonds the sheath to the core is part of a polymer skin which, in the case of a joint-replacement device, conforms to and fills the space of a bone cavity in which the device is received. In a preferred embodiment of the prosthesis device, the outer geometry of the skin conforms to a spiral-like cavity formed in a femur by removal of soft cancellous material only, as described in the earlier, co-pending application.

In forming the beam according to the method of the invention, there is provided an elongate core formed of continuous fibers extending substantially along the length of the core and embedded in a polymer matrix. In forming the exemplary hip-joint replacement device, the core is prepared by forming a series of planar fiber/composite layers containing a 35-55 degree bend. In each layer, the fibers are arranged in a substantially uniform density pattern which follows the curve in the layer. The layers are laminated together to form a block in which all of the fibers have substantially the same axial orientation, and the fused block is machined to form the neck, stem and tapered section of the core.

The core is encased in a sheath made up of filaments which encircle the core in a helical pattern along its length. The sheath is then embedded in a thermoplastic polymer capable of fusion to the core, and a polymer skin is formed about the core and sheath. In one embodiment, the sheath may be embedded in polymer and fused to the core before forming the outer polymer skin. In a second embodiment the sheath is embedded in the polymer and the outer skin formed in a single injection molding step.

These and other objects and features of the invention will become more fully apparent when the following detailed description of the invention is read in conjunction with the accompanying drawings.

BRIEF DESCRIPTION OF THE DRAWINGS

FIG. 1 is a frontal sectional view of a proximal portion of a right femur fitted with a prosthetic device constructed according to an embodiment of the invention;

FIG. 2 is a side sectional elevational view of the FIG. 1 prosthetic device, as viewed from the right in FIG. 1, and with the ball-joint member removed;

FIGS. 3-8 show a series of cross-sections taken along lines 3—3, 4—4, 5—5, 6—6, 7—7, and 8—8, respectively in FIG. 1 and shown in plan view with shallow depth of field;

FIG. 9 shows in plan view a fiber/polymer composite layer used in forming a core in a curved-stem structural beam, such as the prosthetic device shown in FIGS. 1 and 2;

FIG. 10 is a perspective view of a laminate block formed by laminating a series of layers of the type shown in FIG. 9.

FIG. 11 shows in elevational view the core of the prosthetic device of FIGS. 1 and 2, formed by machining the laminate block of FIG. 10;

FIG. 12 shows the appearance of the FIG. 11 core having a braided sheath encasing the core's stem; and FIG. 13 is an enlarged sectional view of an upper portion of the prosthetic device of FIG. 1 taken along the longitudinal axis of the core with polymer skin removed.

DETAILED DESCRIPTION OF THE INVENTION

The beam construction and method of the invention will be described and illustrated with respect to a hip-joint replacement prosthetic device, such as the device shown at 12 in the figures. This embodiment illustrates several features and advantages of the invention which are related both to the beam's ability to resist bending and torsional stresses, and to the transfer weight loading stresses to a bone cavity in which the beam is received. The more general constructional features of the beam of the invention will be apparent from the description of device 12, and of its method of manufacture, as will uses and advantages of the beam in a variety of settings.

A. Beam Construction

FIG. 1 shows, in frontal, sectional view, device 12 attached to the proximal (upper end) portion of a human right femur 14. The device generally includes a neck 16 and an elongate stem 18 which is carried in an intramedullary cavity 20 formed in the bone, and defined by a wall of densified cancellous bone contained within the cortical shell in the proximal bone end. The spiral-like shape of the cavity and the outer shape of the stem which conforms to the cavity are discussed in detail in co-pending patent application for "Femoral-Joint Prosthesis Device". Here it is sufficient to note that the outer surface of the stem is in intimate contact with the cavity over much of its area. The relatively large contact interface between the stem and the bone cavity produces better seating in, and attachment to, the bone, and allows more physiological load transfer from the stem to the bone. The stem surface configuration, as it relates to seating and load transfer within cavity 16, will also be discussed below.

Considering first the construction of device 12, an elongate core 22 in the device includes a neck 24, an elongate curved stem 26, and a tapered section 28 connecting the neck and the stem, as seen best in FIG. 11. The angle formed in the stem, as measured between an axis 30 extending along the lower, distal portion of the stem and an axis 32 extending axially through the center of the neck, and designated by angle A in FIGS. 1 and 11, is preferably between about 35 and 55 degrees. The relative cross-sectional dimensions of the neck, tapered section and stem along the length of the core are apparent from the series of cross sections shown in FIGS. 3–7. As seen, the cross-sectional area of the stem is less than about one-quarter that of the neck. In a typical prosthesis device, the neck has a diameter of between about 16 and 18 mm, and stem a diameter ranging from about 2 to 4 mm at its distal end, to up to twice that diameter or more at its juncture with the tapered section. The tapered section mates the neck and stem by a continuously decreasing taper over a relatively short portion of the core, i.e., a length which is substantially shorter than the stem itself. The tapered section and stem 26 in the core form the interior support of stem 18 in the device, and neck 24 in the core forms the main body of neck 16 in the device.

According to an important feature of the invention, the core is a fiber/resin composite formed of continuous-filament fibers oriented substantially along the length of the core, and extending continuously between the ends of the core. As will be described below, the core is formed in such a way that the fibers are disposed at a relatively uniform density throughout the core, and with little or no fiber distortion along the length of the core, and particularly in the bend region of the core stem. The continuous filaments in the core are carbon fibers, such as those which are supplied commercially for use in fiber/resin composites. A variety of filament thicknesses are suitable, although filaments with diameters between about 5 and 10 microns are preferred because of commercial availability and ease of handling. One preferred core is formed of carbon fibers obtained from Hercules Corp. (Magnat, UT) and having fiber diameter sizes between about 7 and 9 microns.

The resin used in forming the core is a thermoplastic polymer resin which, when formulated with carbon fibers at a fiber/resin ratio of up to 1:1 volume percent or more, produces a composite having desired tensile strength and elastic bending modulus characteristics as described below in Section B. Exemplary resins include polysulfone, polyethersulfone, polyarylsulfone, polyphenylene sulfide, polycarbonates, aromatic polyamides, aromatic polyamideimides, and thermoplastic polyimides. Properties and methods of formulating and molding thermoplastics are described generally in Schwartz, M. M., *Composite Materials Handbook*, (1984) McGraw Hill, N.Y., N.Y. One preferred resin is polysulfone. The fibers are included in the composite, at a volume ratio of at least about 30%, and more preferably between about 50%–60%. In general, the greater the volume (or weight) ratio of fibers, the greater the tensile strength and bending modulus of elasticity.

The stem and tapered section of the core are encased in and bonded to a sheath 34. With reference to FIG. 12, the sheath is formed of braided or woven filaments, such as filaments 36, which encircle the stem in a helical pattern extending along the encased portion of the core. The filaments preferably crisscross the core's long axis at about 45 degree angles, i.e., at angles intermediate between the long axis of the core, and cross-sectional planes along the length of the core. The density of braid weave in the sheath can be varied according to the weave spacing and thickness or number of filaments in the woven filament strands. The sheath preferably is formed of one layer of tightly braided filaments having a thickness of about 20 mils.

The fiber sheath acts to strengthen the device against torsional loading, as will be discussed in Sections B and C. The shear strength and modulus properties which give optimal performance in the device can be selected according to the filament density and thickness of the weave. The sheath also acts to prevent external cracks in the device from spreading beyond their point of contact with the sheath.

The sheath is embedded in a thermoplastic resin which forms a covering or skin 38 over the core and sheath. The skin resin is one which can be heat fused to the core under suitable pressure and temperature conditions, and preferably one which can be applied to the core and sheath by injection molding. The thermoplastic resins mentioned above are suitable, to the extent the resin is compatible with the core resin. In the particular embodiment mentioned, the skin is a polysulfone resin applied by injection molding. The resin mix used in forming the skin may contain a selected volume percentage of short randomly oriented carbon filaments, to increase the rigidity and strength properties of the skin.

The skin serves three purposes: First, it provides an embedding matrix for the sheath, creating a resin/filament composite shell which can be heat fused to the core. The stem thus acquires the combined strength and elastic modulus properties of both the internal core composite, with its longitudinally braided oriented fibers, and the sheath layer, with its fibers extending helically along the length of the stem. Secondly, the core contributes a relatively large volume of material, in relation to the core and sheath, having a low bending and torsional elastic modulus. The result is that the overall elastic modulus of the stem is much smaller, i.e., more like that of soft cancellous bone, than an equivalent-volume stem formed of a resin/fiber composite alone. Finally, the skin gives the stem a shape and size which conforms to and fills the space of a bone cavity in which the stem is received.

Regarding the last point, the skin preferably has a surface geometry which is designed for twist-in, complementary fit into the special type of intramedullary femur cavity which has been described in the earlier filed co-pending patent application. This cavity is produced by removing relatively soft cancellous bone material from the intramedullary region of the bone, leaving a wall of densified cancellous bone contained within the cortical shell and characterized by a 15–30 degree twist on progressing toward the proximal femur end.

The outer surface geometry of the skin which conforms to this type of cavity can be appreciated with reference to FIG. 1, and to FIGS. 3–8 which show a series of cross sections taken along the length of the device. As seen in FIG. 1, the outer surface of the stem has maximally spaced infero-medial and supero-lateral curves 42, 44 respectively extending along the length of the stem. The surface of the stem is characterized by a surface rotation which carries supero-lateral curve 44 between about 15°–30° forward (in an anterior direction with the device in operative position) with respect to infero-medial curve 42, on moving upward along the stem's proximal portion. This rotation is seen in FIGS. 3–8, where the angle of movement of the supero-lateral curve is compared with a lateral axis 46 which extends in a substantially side-to-side direction when the device is operatively placed in a bone site. The surface-twist geometry of the stem necessitates a right and left prosthesis, because the rotation of the prosthesis cross-section on one side is counterclockwise and on the other is clockwise.

Completing the description of device 12, the neck 16 includes a tapered thimble 50, carried on the neck of core 22, as seen in FIG. 1. Thimble 50 is adapted to carry a ball-like hip-joint head, or member 52 (FIG. 1), which is received by press fit in a tapered cavity 54 formed in the member. The thimble and cavity may have various complementary configurations, e.g., elliptical, to prevent the member from rotating on the thimble.

The thimble has a series of fingers, such as finger 56 seen in FIG. 13 which are used in anchoring the thimble to the neck of the core. These fingers are pressed down against the tapered section of the core, after placing the thimble of the core neck, by a retaining ring 58 which is slipped over the lower portion of the thimble from the stem end of the device. The ring acts to secure the thimble to the head, allowing a distraction force—such would be necessary, for example, to remove a head from the thimble during surgery—to be applied to the thimble without pulling the thimble off the core. An annular lip 60 on the retaining ring can be used for removing the prosthesis device from a bone cavity during surgery, either to replace or reposition the device in the cavity.

With reference now to FIG. 2, the neck with the attached thimble are inclined about 3°–15° forward (toward the anterior of the body) with respect to an axis 62 which extends through the stem's lower proximal region. This inclination, or anteversion, functions to place ball member 52 at a position which closely approximates the average position occupied by the natural head in the femur. It is noted, however, that actual variations in the head positions in a large population range from about 38° anteversion to 20° retroversion. In cases of more extreme retroversion, it may be advantageous to incline the thimble (and attached ball member) in a more neutral position.

B. Beam Construction Methods

The beam construction method of the invention follows the steps of: (a) providing a continuous-filament core, (b) forming a sheath about the core, (c) embedding the sheath in a polymer, to fuse the sheath to the core, and (d) forming the outer polymer skin. These steps will now be detailed with respect to the construction of a hip-replacement prosthetic beam, specifically device 12. It will be understood that the construction methods are applicable for constructing other types of straight and curved beams useful in both prosthetic and more general support applications. The construction method is illustrated particularly in FIGS. 9–12.

The core is preferably formed from a laminate block, such as block 64, shown in FIG. 10. The block is made up of a series of fused layers, such as layers 66, 68, each having the general construction shown in plan view in FIG. 9. As seen, the planar dimensions of the layer encompass the shape of the core, shown in dotted lines at 22, which is to be cut from the laminate block.

Layer 66, which is representative, can be formed conveniently by mold injection techniques. Initially, a bundle of continuous carbon fibers or filaments 74, such as described above, are laid down in a mold (defined by the outer dimensions of layer 66), such that the fibers extend continuously between the opposite ends of the mold at a relatively uniform filament density throughout. As can be appreciated from the figure, the fibers can be laid out without significant fiber distortion, particularly in the bend region of the mold, if the fibers on the outer (left) side of the layer are longer than those on the inner layer side. This is in contrast to the distorted condition of the fibers which would occur if the fibers were first laid out along a straight line in a rectangular layer, and the layer then bent after resin molding.

The density of fibers in the layer is selected to produce desired strength and tensile modulus of elasticity in the finally formed core. In a preferred embodiment, the core has a tensile strength of between about 150–200 ksi ($10^3$ psi), and a tensile or bending modulus of elasticity of between about 12 and 20 msi ($10^6$ psi). These values are consistent with a carbon/polysulfone resin containing between about 40–60 volume percent carbon fibers.

The individual layers, which have a preferred thickness of between about 0.125 and 0.150 mm, are stacked together and heated in a mold under temperature and pressure conditions which melt the resin and fuse the laminate into a unitary block, such as block 64. Such fusing conditions are well known to those in the art, and typically involve pressures in the range of 600–1500 psi, and temperatures in the range between about 400°–700° C. The block has a final thickness which is roughly the same as the end dimensions of the individual layers.

The block is then machined by conventional methods to form the core, such as core 22 seen in FIG. 11. According to an important advantage of the block construction, since all of the fibers follow the bend in the block, the only significant group of core fibers which are severed in the machining operation are those in the tapered section, with substantially all of the fibers in the stem region of the core extending into and through the central region of the neck.

FIG. 12 illustrates the next step in the beam construction, in which a sheath, such as sheath 34, is formed over the stem and tapered section of the core. The sheath can be formed conventionally by weaving or preferably braiding continuous carbon filaments directly over the stem and tapered section of the core, or over a core-like mandrel. Commercial braiding machines, such as those used in forming the shielding wire in a coaxial cable, are suitable for this operation. The braid produced by such machines has the desired pattern of filaments which encircle the stem in a helical pattern extending along the length of the core. The carbon filaments used in forming the braid are similar to those used in the core, and have a preferred filament thickness between about 7 and 9 microns.

As indicated above, the density and thickness of the weave in the sheath can be selectively varied to produce desired torsional strength and modulus of elasticity characteristics in the stem. In the specific hip prosthesis device under consideration, the sheath, when embedded with thermoplastic polymer and fused to the core, has a shear strength of between about 10 and 14 ksi, and a shear modulus of elasticity of between about 2 and 6 msi ($10^6$ psi). These values are consistent with a sheath/polysulfone resin shell about 20–30 mils thick and containing between about 40–55 volume percent carbon fibers.

In one preferred method for embedding the sheath in a thermoplastic resin, the sheath and core are soaked one or more times in a solution of the polymer in a volatile organic solvent or solvent system. One exemplary polymer solution polysulfone is a 10% weight percent solution in dichloromethane. After each soaking, the sheath is dried to remove solvent, forming a progressively thicker layer of resin carried on the sheath. After a sufficient buildup of material, the core and sheath are placed in a mold and subjected to temperature and pressure conditions which cause the resin buildup in the sheath to fuse with the core. The method produces substantially complete infusion of resin into the sheath and bonding to the core. The resulting core and sheath construction is now ready for a final injection molding step used in forming the outer polymer skin. Alternatively, the steps of embedding the sheath in resin and forming the polymer skin can be carried out in a single injection molding technique, where material injected into the mold at high pressure is effective to infuse the sheath and envelop the core prior to curing the polymer skin. Although this approach avoids a separate infusion step, it may produce voids and other irregularities at the sheath/core interface due to incomplete polymer infusion. The latter problem can be controlled in part, by heating the core prior to and during polymer injection into the mold.

Following the embedding step, thimble 50 is placed over the core neck and fastened to the core by means of ring 58, as described above. The construction is now ready for the final injection molding step for producing the polymer skin. This procedure is carried out according to known injection molding techniques. The injection mold is shaped to form a polymer skin having desired volume and surface geometry features, as discussed above, and constructed to support the mold and sheath at a desired position and orientation to support the mold and sheath at a desired position and orientation during the molding process. In this regard, it is noted that the relatively small diameter core stem allows the core to be tilted slightly out of plane of the mold, i.e., the plane which contains the bend in the core stem can be tilted out of the plane which contains the bend in the corresponding bend in the mold. The net effect of this tilting is to place the neck in the core at a selected anteversion angle, preferably between about 5–15 degrees, as seen in FIG. 2.

The polymer used in forming the skin is preferably the same as that used in embedding the sheath and forming the core, such as polysulfone. The resin may be prepared to contain chopped fibers, where added strength or resistance to tearing is desired.

C. Mechanical Properties of the Beam

The mechanical properties of the beam can be understood in terms of the composite properties of the core, braid and skin elements which make up the beam. The properties of particular interest are (a) bending and shear strength, (b) elastic moduli in bending and shear, and (c) load transfer, particularly load transfer to a surrounding bone cavity.

The principal bending strength of the beam is provided by the core, whose bending strength is generally comparable to or greater than metal alloys, which are currently used in prosthetic devices. For example, the tensile strength (measured in the direction of fiber orientation) of a standard dimension 57% carbon fiber/polysulfone composite is about 180–200 ksi, as compared with about 90–125 ksi for a variety of alloys. Since the bending strength is largely defined by the core, and the strength along the length of the core is related to core thickness, the device is characterized by very high strength in its neck, which must bear all of the weight loading applied to the bone, and substantially lower strength within the bone region, where loading forces can be distributed to and absorbed by the bone. The tapered section provides a means for reducing the load bearing capacity of the core over a relatively short distance within the upper region of the bone, without an actual discontinuity in load bearing capacity, as would be the case if the smaller stem were mated directly to the larger neck.

The tensile strength of the core decreases markedly as the direction of applied force shifts from bending and axial compression forces applied in the direction of fiber orientation, and torsional or twisting forces, applied in the direction which is essentially perpendicular to fiber orientation. For example, in the above carbon fiber/polysulfone complex, tensile strength falls from about 150–200 ksi for purely bending forces to about 7 ksi for purely torsional forces.

The strength characteristics in the core are reflected by the tensile and shear moduli of elasticity, which give a measure of the stiffness of the core, and are defined as the slope of the linear portion of the stress-strain curve. A core formed in accordance with the invention, such as a carbon filament/polysulfone composite core has a bending modulus of between about 15–20 msi, and a torsional bending modulus (the response to the core of torsional force) of less than about 1 msi.

The shear strength of the stem region is provided largely by the composite sheath whose filaments are dispersed helically about the stem. It can be appreciated that the helical fibers are stretched in torsion but not in bending or compression, so that the sheath strengthens and stiffens the core primarily in shear modes. Specifically, the sheath has a typical tensile modulus of about 1 msi or less, and a shear modulus of between about 4–7 msi. In the neck region of the device, shear strength is provided by the greater thickness of the neck.

The strength of the polymer skin is relatively low—about 10 ksi—for both bending and torsional forces and thus makes a relatively small contribution to overall strength in the stem, particularly in bending mode. Although the strength of the skin can be increased by addition of randomly oriented, short fibers, more advantageous load transfer properties may result if pure polymer is used, as will be discussed below. The modulus of elasticity of the material, in both tensile and torsional modes, is less than about 1 msi.

In operation, normal weight loads which are applied to the hip prosthesis are carried initially in ball joint and connected neck of the device. These loads, which may include bending, axial compression and torsional loads, are transferred to the upper joint region of the bone, in the region corresponding substantially to the tapered section of the prosthesis stem. It can be appreciated that the relatively thick neck in the device provides high tensile and shear strength in the unsupported neck, while the tapered section provides a sharply reduced strength and stiffness as a major portion of the load is transferred to the upper end of the bone. Within the stem region of the prosthesis, bending and tensile strength is provided largely by the core with its axially oriented fibers, while shear strength is contributed largely by the sheath with its helically arranged fibers.

As noted above, the distribution of forces in the underlying cortical region and prosthesis stem region is determined by the relative elastic moduli of the bone and prosthesis components. Ideally, for physiological loading, it is desirable to have the load distribution between the stem and surrounding cortical bone roughly match that of the natural bone. That is, the load distribution in the stem should closely match that of the soft cancellous bone region which the stem has replaced. Under these conditions, there is minimal stress protection of the cortical bone by the prothesis, and high stresses are not concentrated in the bone region near the tip of the stem. In analyzing load distribution between prosthesis and bone, bending, compression, and torsional forces will be considered. General load distribution theory upon which the following discussion is based is given in Timoshenko and Young, Elements of the Strength of Materials, D. Van Nostrand (1968), 5th edition.

The load distribution in response to bending loads is generally described by the area moment of inertia which is defined as the product of the elastic modulus in bending and the fourth power of the cross-sectional radius of the body which carries the load. For a series of concentric load-bearing components, the portion of the load carried by each component is determined as the area moment of inertia of that component divided by the sum of the area moments of all of the components. Making some simplifying assumptions about the shape of the cortical bone regions, and using elastic modulus and radii values for the stem components and the bone which are given above, it is calculated that less than about one-fifth of the total load is borne by the stem. The relatively low loading on the stem is due primarily to the low-modulus, polymer skin which has load distribution characteristics similar to that of soft cancellous bone, and which makes a major contribution to the total loading in the stem by virtue of the fourth power dependence on radius.

Shear and axial compressional loading can be similarly determined from the relative magnitudes of the shear and compressional moments of the stem components and surrounding cortical bone region. Here the critical load bearing property for shear is the shear moment, defined as the product of the shear modulus and the cross-sectional area and tensile moment defined as the product of tensile elastic modulus and cross-sectional area. For both shear and tensile loading, the portion of load borne by each component is calculated as the moment for that component divided by the total moments of all of the stem components and the surrounding cortical bone. Since the terms in both moments are dependent on the square of the cross-sectional radii, rather than the fourth power as in the area moment term in bending, the relative contribution of the low modulus outer skin will be less relative to the higher modulus core and sheath components than in bending. Nonetheless, it can be appreciated that the relatively large radius of the low-modulus skin acts to reduce total loading on the stem substantially. Also, in torsional loading, it is recalled that the shear modulus of the core itself is quite low, so the major loading moment in torsion is the thin sheath layer. Thus, in bending, loading on the stem is low due to the fourth power dependence of the outer skin, and in torsion, loading is low due to the low-moduli of both skin and core components.

The stem of the invention is also characterized by a low modulus of compression in directions normal to the long axis of the stem. More specifically, the modulus of elasticity of the sheath and core structure is of the same general magnitude as that of the polymer skin. This is because neither the axial fibers in the core nor the helical fibers in the sheath are oriented to resist compression in directions normal to the stem axis. As a result, reactive load forces which are applied to the stem by the bone, particularly in bending, are distributed relatively evenly between the interior core and sheath and the polymer skin. The core thus has little tendency to cut against the polymer, as would be the case if the core were much stiffer in side-directed compression.

From the foregoing, it can be appreciated how various objects and features of the invention are met. The beam of the invention is adapted for support in both bending and torsional load, and the beam can be constructed to have selected shear and tensile properties, according to the method of the invention, by selected changes in the core and sheath composition and changes in the relative cross sectional features of the beam components. Thus, for example, if greater shear strength is needed, the sheath filament density can be increased, while filament density in the core can be adjusted to achieve desired tensile strength. The composite beam construction is relatively lightweight, and thus advantageous in medical and other applications.

In use as a weight-bearing joint prosthesis device, the beam modulus characteristics provide favorable loading and load distribution characteristics when compared with prior art prostheses devices. In particular, the relatively large area and low modulus of the outer skin component of the beam, and the low shear modulus of the core, combine to reduce load distribution in the stem in both bending and torsional loading. As a result, the surrounding cortical bone experiences more physiological loading, and localized stresses at the distal end of the stem are minimized. Further, the relatively well matched elastic moduli of the stem components in lateral compression prevents cutting action of the core and sheath against the outer skin over extended periods.

The outer skin in the beam may be readily designed to a variety of surface configuration and space filling needs. For example, in a hip-joint prosthesis device, the skin can be designed to fill a selected size bone cavity, and its surface configuration can be molded with the spiral-like surface described above for twist-in insertion into femur cavity formed by removal of soft cancellous material only.

While preferred embodiments of the invention have been described herein, it will be apparent that various changes and modifications can be made without departing from the spirit of the invention.

We claim:

1. A thin core beam adapted for implantation within a bone to support a load capable of applying bending and torsional loading forces, comprising
   an elongate solid core formed of continuous-filament fibers oriented substantially along the length of the core and embedded in a polymer matrix,
   encasing the core, a sheath formed of filaments which encircle the core in a helical pattern extending along the core's length, and
   a thermoplastic polymer skin heat fused to and covering the core, said skin having said sheath embedded therein, said skin comprising a larger volume than the sum of the volumes of the core and the sheath and having a low bending and torsional elastic modulus relative to said core and sheath, and the skin, core and sheath dimensions selected so that when implanted, the bending load force distribution between the device and the surrounding bone approximates that of natural cancellous bone.

2. The beam of claim 1, wherein the fibers in the core and sleeve are continuous filament carbon fibers, and the core and skin polymers are thermoplastic polymers.

3. The beam of claim 1, which has a bend of more than about 30 degrees, and the continuous filament fibers in the core are non-distorted and follow the bend in a relatively uniform-density pattern.

4. The beam of claim 1, for use as a joint replacement prosthetic device adapted to be received in an elongate intermedullary bone cavity, wherein the core includes a stem portion which is covered by said sheath and skin and which is adapted to be received in such cavity, and a neck adapted to support a joint replacement member.

5. The beam of claim 4, wherein said stem portion includes an elongate distal stem whose cross-sectional area is less than about one-fourth that of the neck, and a tapered section which mates the neck to the stem and whose length is substantially less than that of the stem.

6. The device of claim 5, wherein the core has a bending elastic modulus between about $10-25 \times 10^6$ psi, and a torsional elastic modulus of less than about $1 \times 10^6$ psi, the polymer-embedded sheath has a tension elastic modulus of less than about $2 \times 10^6$ psi and a shear elastic modulus between about $2-6 \times 10^6$ psi, and the skin surrounding the sheath has a bending elastic modulus less than about $1 \times 10^6$ psi.

7. The beam of claim 5, for use as a femoral-side joint replacement, wherein the distal stem and surrounding skin has a medial-side bend of between about 40-50 degrees, and the continuous filament fibers in the core are relatively non-distorted and follow the bend in a relatively uniform-density pattern.

8. The beam of claim 7, wherein the bend in the distal stem lies in a first plane which is offset from a second plane containing the bend in the skin, to produce a 3°-15° anteversion of said neck with respect to the second plane.

9. The beam of claim 7, wherein the beam is shaped and dimensioned to conform to and fill an elongate intramedullary cavity defined substantially by a wall of densified cancellous bone containing within the cortical shell in the proximal end of a femur.

10. The beam of claim 9, wherein the outer surface of said skin defines maximally spaced inferomedial and superomedial surface curves, and which is characterized by a surface rotation which carries the superolateral surface curve about 15°-30° forward with respect to the inferomedial surface curve, on progressing along the beam toward the neck, with the device in operative position.

11. A thin core construction in a femoral-side hip joint replacement device having an elongate curved stem adapted to be received in an elongate, intramedullary cavity in a femur, and a neck adapted to support a ball-like joint member at the femur's proximal end, said construction comprising
    an elongate solid core formed of continuous-filament fibers oriented substantially along the length of the core and embedded in a polymer matrix, including said neck, an elongate distal stem whose cross-sectional area is less than about one-quarter that of the neck, and a tapered section which mates the neck to the stem and whose length is substantially less than that of the stem,
    encasing the core, a sheath formed of filaments which encircle the core in a helical pattern extending along the core's length, and
    a thermoplastic polymer skin shaped to conform to and fill said femur cavity, said skin heat fused to and covering the core and having said sheath embedded therein, said skin comprising a larger volume than the sum of the volumes of the core and the sheath and further having a low bending and torsional elastic modulus relative to said core and sheath, and the skin, core and sheath dimensions selected so that when implanted, the bending load force distribution between the device and the surrounding bone approximates that of natural cancellous bone.

12. The construction of claim 11, wherein the stem has a bending elastic modulus between about $12-20 \times 10^6$ psi and a torsional elastic modulus of less than about $1 \times 10^6$ psi, the polymer-embedded sheath has a bending elastic modulus of less than about $1.5 \times 10^6$ psi and a torsional elastic modulus between about $4-8 \times 10^6$ psi, and the skin surrounding the sheath has a bending elastic modulus less than about $1 \times 10^6$ psi.

13. The construction of claim 11, for insertion into an intramedullary cavity defined substantially by a wall of densified cancellous bone contained within the cortical shell in the proximal end of a femur, wherein the outer surface of said skin defines maximally spaced inferomedial and superomedial surface curves, and which is characterized by a surface rotation which carries the superolateral surface curve about 15°-30° forward with respect to the inferomedial surface curve, on progressing along the beam toward the neck, with the device in operative position.

14. The construction of claim 11, wherein the distal stem and surrounding skin has a medial-side bend of between about 40°-50°, and the continuous filament fibers in the core are relatively non-distorted and follow the bend in a relatively uniform-density pattern.

15. The construction of claim 14, wherein the bend in the distal stem lies in a first plane which is offset from a second plane containing the bend in the skin, to produce a 3°-15° anteversion of said neck with respect to the second plane.

* * * * *

UNITED STATES PATENT AND TRADEMARK OFFICE
CERTIFICATE OF CORRECTION

PATENT NO. : 4,750,905

DATED : June 14, 1988

INVENTOR(S) : Koeneman et al.

It is certified that error appears in the above-identified patent and that said Letters Patent is hereby corrected as shown below:

Column 4, line 30 delete "sectional"

Signed and Sealed this

Twenty-fifth Day of October, 1988

Attest:

DONALD J. QUIGG

*Attesting Officer*    *Commissioner of Patents and Trademarks*